US012039853B2

(12) United States Patent
Payment

(10) Patent No.: US 12,039,853 B2
(45) Date of Patent: *Jul. 16, 2024

(54) DETECTING LIFE BY MEANS OF CO2 IN AN ENCLOSED VOLUME

(71) Applicant: Venturi, LLC, Huntsville, AL (US)

(72) Inventor: Benjamin Victor Payment, Huntsville, AL (US)

(73) Assignee: Venturi, LLC, Huntsville, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/084,281

(22) Filed: Dec. 19, 2022

(65) Prior Publication Data

US 2023/0123053 A1 Apr. 20, 2023

Related U.S. Application Data

(63) Continuation of application No. 17/099,498, filed on Nov. 16, 2020, now Pat. No. 11,538,325, which is a continuation of application No. 16/235,648, filed on Dec. 28, 2018, now Pat. No. 10,839,666, which is a continuation of application No. 15/812,846, filed on Nov. 14, 2017, now Pat. No. 10,169,975.

(51) Int. Cl.
| G08B 21/12 | (2006.01) |
| G01K 1/024 | (2021.01) |
| G01N 33/00 | (2006.01) |
| G08B 21/18 | (2006.01) |
| G08B 21/22 | (2006.01) |
| G08B 25/00 | (2006.01) |
| G08B 25/10 | (2006.01) |
| G08B 29/18 | (2006.01) |

(52) U.S. Cl.
CPC ............. *G08B 21/12* (2013.01); *G01K 1/024* (2013.01); *G01N 33/004* (2013.01); *G08B 21/182* (2013.01); *G08B 21/22* (2013.01); *G08B 25/006* (2013.01); *G08B 25/10* (2013.01); *G08B 29/181* (2013.01)

(58) Field of Classification Search
None
See application file for complete search history.

(56) References Cited

U.S. PATENT DOCUMENTS 5,676,913 A * 10/1997 Cirillo .................... B01D 53/75
423/247
6,388,410 B1 * 5/2002 Hohn .................. B60R 25/1001
318/449

(Continued)

*Primary Examiner* — Fekadeselassie Girma
(74) *Attorney, Agent, or Firm* — Angela Holt; Bradley Arant Boult Cummings LLP

(57) ABSTRACT

In a system and method for detecting carbon dioxide in an enclosed volume, a CO2 detection system is triggered to awaken from a deep sleep state. Once awake, the system queries system sensors to determine the current system parameters, including current CO2 level and temperature. Current and expected CO2 decay rates are calculated, and the system determines whether the current CO2 decay rate is within an expected normal range for an unoccupied enclosed volume. If the volume is static, i.e., not moving, and the CO2 rate is rising and the temperature is rising, a series of alerts are sent to contacts previously set up by the user. If the alerts are not cleared by a user, emergency management personnel are notified.

5 Claims, 7 Drawing Sheets

(56) References Cited

U.S. PATENT DOCUMENTS

| | | | | |
|---|---|---|---|---|
| 6,485,081 | B1* | 11/2002 | Bingle | E05B 81/54 |
| | | | | 292/DIG. 43 |
| 6,768,420 | B2* | 7/2004 | McCarthy | H03K 17/955 |
| | | | | 340/425.5 |
| 6,810,309 | B2* | 10/2004 | Sadler | B60R 25/04 |
| | | | | 701/1 |
| 7,348,880 | B2* | 3/2008 | Hules | B60R 25/1004 |
| | | | | 340/425.5 |
| 7,646,287 | B2* | 1/2010 | Hayashi | B60R 25/1004 |
| | | | | 340/426.25 |
| 7,656,287 | B2* | 2/2010 | Albert | G08B 21/0211 |
| | | | | 340/517 |
| 7,768,380 | B2* | 8/2010 | Breed | G06V 40/10 |
| | | | | 340/5.82 |
| 8,035,508 | B2* | 10/2011 | Breed | H01Q 1/3291 |
| | | | | 709/219 |
| 8,253,553 | B2* | 8/2012 | Wedig | G08B 7/066 |
| | | | | 340/541 |
| 8,378,800 | B2* | 2/2013 | Mackjust | B60R 25/10 |
| | | | | 701/2 |
| 8,590,366 | B2* | 11/2013 | Park | G01N 21/3504 |
| | | | | 73/31.05 |
| 9,470,670 | B2* | 10/2016 | Angeli | G01N 33/0067 |
| 10,145,831 | B2* | 12/2018 | Angeli | G01N 33/004 |
| 10,169,975 | B1* | 1/2019 | Payment | G08B 25/10 |
| 10,839,666 | B2* | 11/2020 | Payment | G08B 25/10 |
| 2005/0038582 | A1* | 2/2005 | Arndt | G08B 21/12 |
| | | | | 701/31.4 |
| 2007/0139170 | A1* | 6/2007 | Higuchi | B60R 25/1004 |
| | | | | 340/426.1 |
| 2011/0296872 | A1* | 12/2011 | Eisenberger | B01D 53/81 |
| | | | | 96/111 |
| 2012/0226418 | A1* | 9/2012 | Veen | B60W 50/16 |
| | | | | 297/217.3 |
| 2013/0194089 | A1* | 8/2013 | Estrada | G08B 21/22 |
| | | | | 340/584 |
| 2015/0054650 | A1* | 2/2015 | Frish | G01M 3/226 |
| | | | | 340/605 |
| 2016/0350096 | A1* | 12/2016 | Pipilas | G06F 8/65 |
| 2018/0139415 | A1* | 5/2018 | Newman | G08B 27/001 |
| 2018/0155556 | A1* | 6/2018 | Subbloie | C22F 1/14 |
| 2019/0088103 | A1* | 3/2019 | Lebron | G08B 21/0277 |
| 2021/0074142 | A1* | 3/2021 | Payment | G01K 1/024 |
| 2023/0123053 | A1* | 4/2023 | Payment | G08B 21/22 |
| | | | | 340/529 |

* cited by examiner

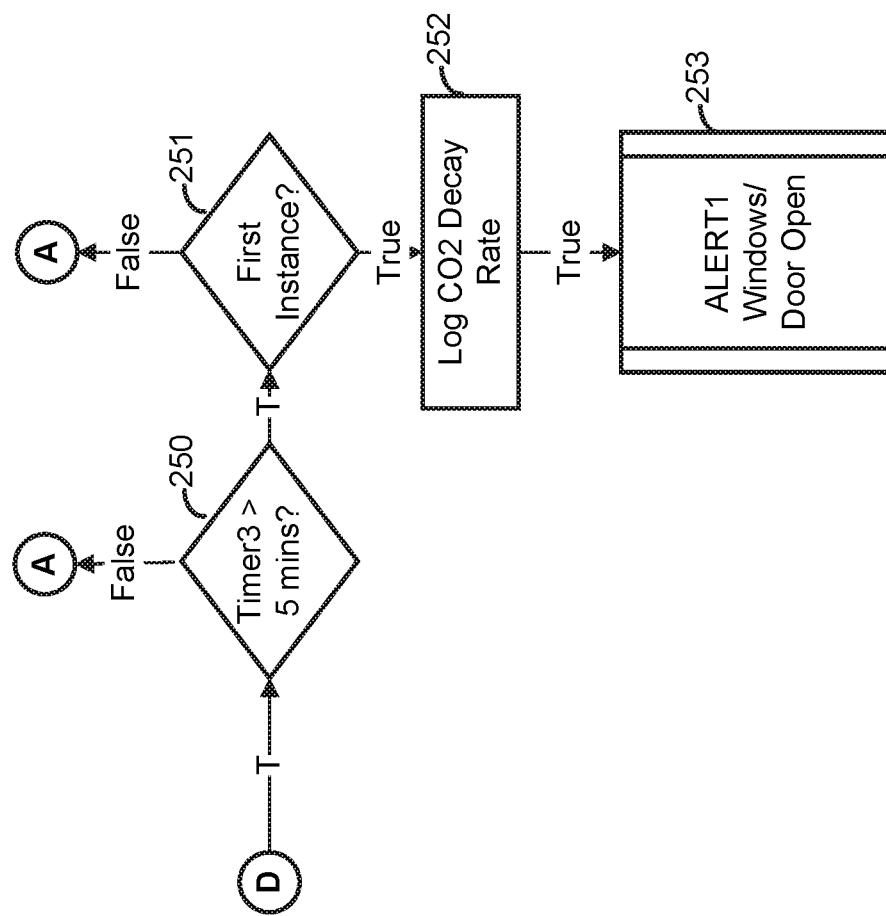

DETECTING LIFE BY MEANS OF CO2 IN AN ENCLOSED VOLUME

REFERENCE TO RELATED APPLICATIONS

This application is a continuation of, and claims priority to, U.S. Non-Provisional patent application Ser. No. 17/099,498, filed on Nov. 16, 2020, and titled "Detecting Life by Means of CO2 in an Enclosed Volume," which is a continuation of, and claims priority to, U.S. Non-Provisional patent application Ser. No. 16/235,648, filed on Dec. 28, 2018, issued as U.S. Pat. No. 10,839,666 and titled "Detecting Life by Means of CO2 in an Enclosed Volume," which is a continuation of, and claims priority to U.S. Non-Provisional patent application Ser. No. 15/812,846, filed on Nov. 14, 2017, issued as U.S. Pat. No. 10,169,975 and titled "Detecting Life by Means of CO2 in an Enclosed Volume." The foregoing applications are incorporated herein by reference.

BACKGROUND AND SUMMARY

The presence of human or animal life and life threatening conditions are detected within a vehicle compartment through the use CO2 and temperature level monitoring. A detection system uses CO2, temperature and vehicle ignition sensors and monitors the rates of change of these inputs. The detection system includes vehicle location identification, and works with or without vehicle power. The detection system can commutate via cellular and/or satellite transceiver(s) to respond to detected events appropriately and may take additional action to respond to hazardous conditions within the vehicle. The detection system will employ a tiered alerting system with escalating severity.

BRIEF DESCRIPTION OF THE DRAWINGS

The disclosure can be better understood with reference to the following drawings. The elements of the drawings are not necessarily to scale, emphasis instead being placed upon clearly illustrating the principles of the disclosure. Furthermore, like reference numerals designate corresponding parts throughout the several views.

FIG. 2D is a continuation of the flow chart of FIG. 2A.

DETAILED DESCRIPTION

Figure 1:
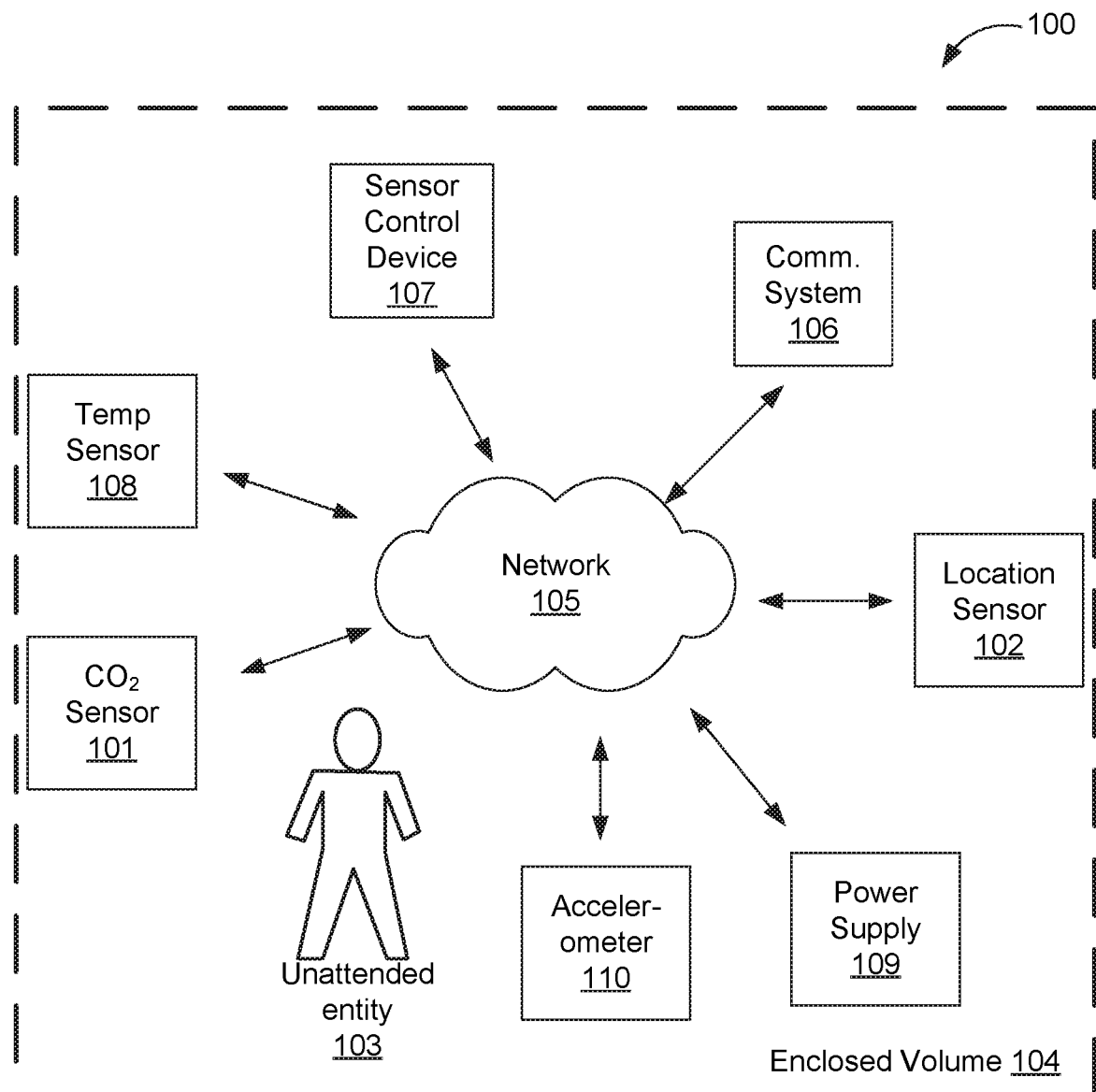
FIG. 1 depicts a system for monitoring CO2 levels in an enclosed volume according to an exemplary embodiment of the present disclosure.
Figure 1:
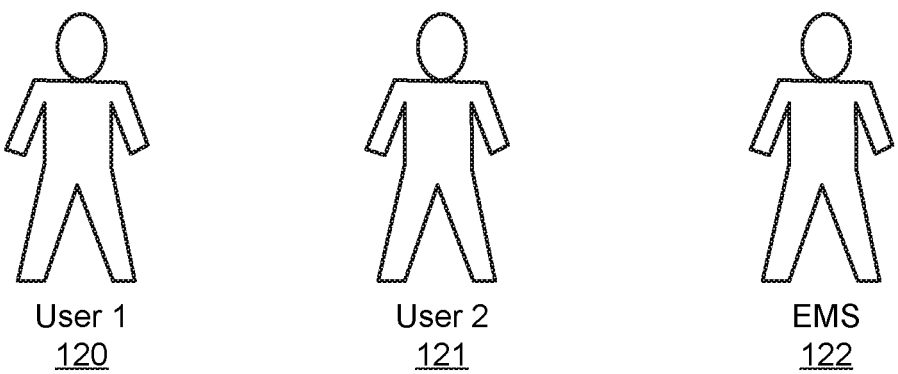

FIG. 1 depicts a CO2 detection system 100 according to an exemplary embodiment of the present disclosure. The system 100 comprises a CO2 sensor 101, a location sensor 102, a temperature sensor 108, a power supply 109, a sensor control device 107, a communication system 106, and an accelerometer 110 (optional), all communicating over a network 105. The system 100 provides alerts when it senses the presence of an unattended entity 103 in an enclosed volume 104, as further discussed herein. The unattended entity 103 may be a child or infant in a car seat, an adult unable to exit the vehicle unassisted, an animal, or the like. The enclosed volume 104 is an automobile or some other enclosure, e.g., mobile enclosures used to transport humans or animals, or static enclosures, such as refrigerators or freezers, or the like, or any reasonably airtight space in which a mammal may be enclosed.

Further, the enclosed volume 104 is one in which a low level of air is exchanged with air that has a known and relatively low concentration of CO2 such as atmospheric air which contains an average CO2 concentration of approximately 400 part per million (ppm). Low air exchange rates are rates on the order of one (1) air exchanges per hours (ACH), which is common in static vehicles. The system can tolerate a range of ACH values. The system uses the ACH value to predict future CO2 levels given the current state of the volume. A tolerance bound around the ACH and associated CO2 prediction allows the system to adapt to different volumes.

In one embodiment, the CO2 sensor 101 comprises a low-power humidity-compensated sensor that is self-calibrating. The CO2 sensor 101 samples the air inside enclosed volume 104, and records the CO2 levels multiple times per second, determining first, second and high order rates of change on CO2 levels, i.e., CO2 levels above a threshold corresponding to nominal atmospheric ~400 parts per million (ppm).

The sensor control device 107 controls the operation of the CO2 sensor 101 and other components in the system 100. Although FIG. 1 shows the sensor control device 107 as a separate component from the CO2 sensor 101, the temperature sensor 108, and other components, multiple components are packaged together into one device in some embodiments. The sensor control device 107 is further discussed with respect to FIG. 3 herein.

The temperature sensor 108 provides temperature data to the sensor control device 107. The temperature sensor 108 is a low-power device in one embodiment. In one embodiment, the sensor control device 107 samples temperature levels via the temperature sensor 108 multiple times per second to determine the temperature in the enclosed volume. The temperature sensor 108 also provides humidity levels, in one embodiment.

The power supply 109 provides power to the system 100. The power supply 109 may be an interface to vehicle power through a cigarette lighter (not shown) or an ODB-II port. Alternatively, the power supply 109 may be the power supplied to the automobile's radio. Other power sources are used in other embodiments, such as solar power or other energy harvesting mechanisms.

The power supply 109 further comprises an internal, rechargeable battery (not shown). This battery will allow the system to operate for at least a week without needing to be recharged, allowing the system to operate without vehicle power and outside of a vehicle. The battery will be automatically recharged when a vehicle is active or power is otherwise available.

The sensor control device 107 will use either a readily available vehicle active signal (available at ODBII and car radio connection) or determine if the vehicle is active using a voltage threshold against the vehicle power. When a vehicle is active it actively charges the vehicle battery increasing system voltage above ~13 VDC. Additionally, modern vehicles generally power cigarette lighters only when the vehicle is active.

The location sensor 102 determines the location of the enclosed volume 104 for transmitting the location when the system 100 issues an alert, as further discussed herein. The location sensor 102 may be a GPS transmitter. The location sensor 102 may comprise a clock used to update system time, and provide the current time to the sensor control device 107.

The communication system 106 in one embodiment comprises a satellite or cellular transceiver or Global System for Modems (GSM) modem that communicates vehicle and occupancy status. The communication system 106 further sends and receives both voice and data communications.

In one embodiment, the accelerometer 110 comprises a standard accelerometer that will trigger in the event a car door is opened or closed. The accelerometer may also trigger when the vehicle is bumped, or someone moves around it, or in other situations. Triggering of the accelerometer "wakes" the system 100, as further discussed herein.

The network 105 may be of any type network or networks known in the art or future-developed, such as the internet backbone, Ethernet, Wifi, WiMax, broadband over power line, coaxial cable, and the like. The network 105 may be any combination of hardware, software, or both.

As further discussed herein, in the illustrated embodiment, when the system 100 detects a dangerous CO2 level, an alert will first go to first user (user 1 120), then to a second user (user 2 121), and then to Emergency Management (EMS 122).

Figure 2A:
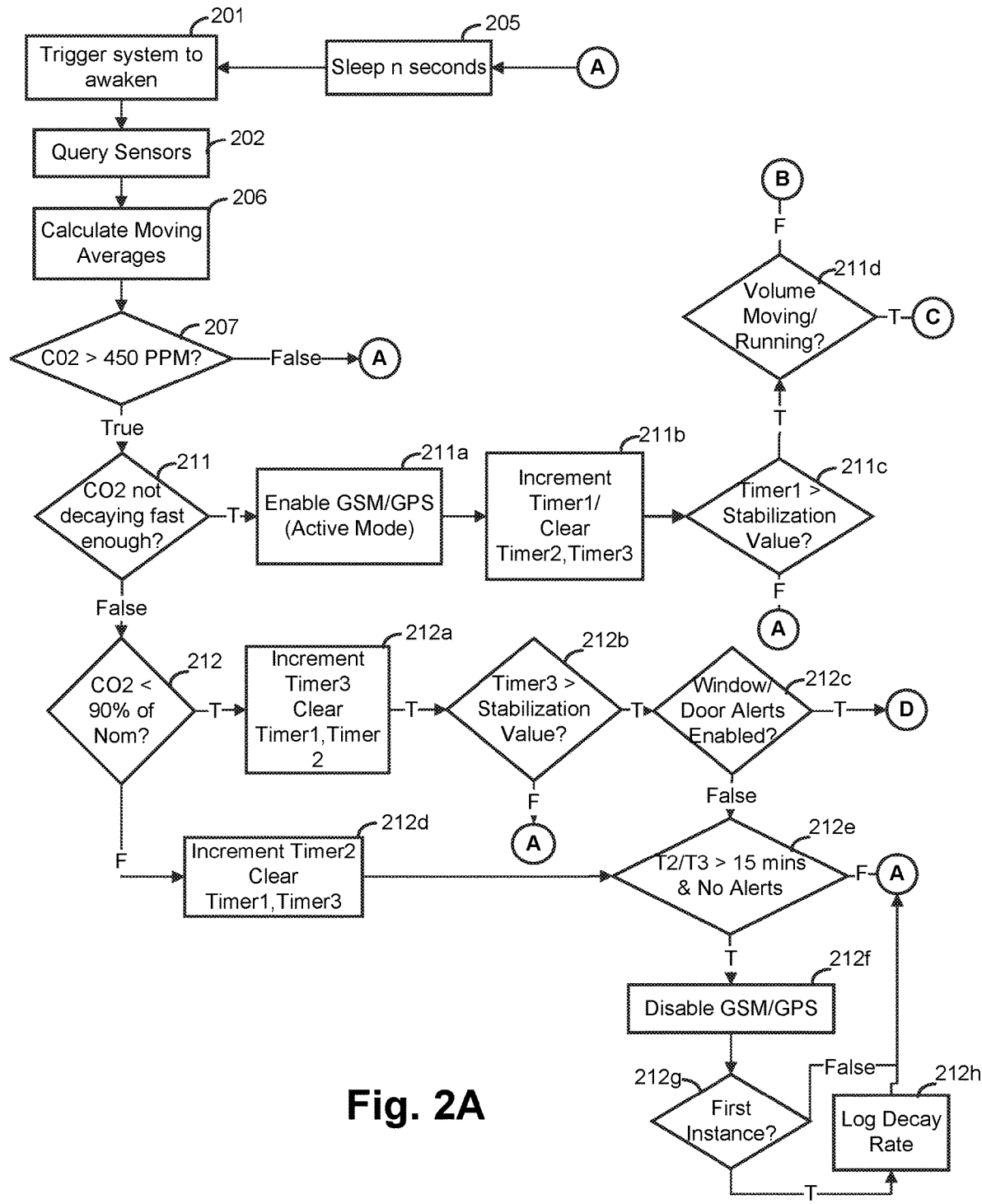
FIG. 2A is a flow chart depicting a method for monitoring CO2 levels in an enclosed volume according to an exemplary embodiment of the present disclosure.

FIGS. 2A, 2B, 2C, and 2D depict a method 200 for detecting CO2 in an enclosed volume, according to an exemplary embodiment of the present disclosure. Referring to FIG. 2A, in step 201 of the method 200, the system 100 (FIG. 1) is triggered to awaken from a "sleep" state. The system polls the sensors at regular time intervals and sleeps between intervals to conserve power. Based on these sensor inputs and associated calculations the system may enter "deep sleep" or "active mode." In one scenario, the accelerometer 110 (FIG. 1) triggers the system 100 to awaken by detecting an event such as a car door opening or closing. In another scenario, the CO2 sensor 101 (FIG. 1) detecting a CO2 level above a threshold triggers the system 100 to awaken, "active mode." In another scenario the system may enter active mode because external power has become available. When the system is in "deep sleep," the communication system 106 and location sensor 102 are unpowered to conserve system power. When the system is triggered to awaken, the communication system 106 and location sensor 102 are powered.

In step 202 of the method 200, the sensor control device 107 queries the sensors to determine system parameters. In this regard, the sensor control device obtains the current CO2 level from the CO2 sensor 101, obtains the current temperature and humidity from the temperature sensor 108, obtains location data from the location sensor 102 (when powered), and the like.

In step 206, the system 100 calculates moving averages needed. In this regard, the sensor control device 107 calculates all of the necessary moving averages, and eliminates noise in the sensor data. Specifically, the moving averages for the current temperature, current CO2 level, current CO2 exponential decay rate, and empirically-determined Air Exchanges Per Hour (ACH). The system 100 will analyze the moving average decay rate of CO2 in the enclosed volume 104. At a time $T_0$ (FIG. 4) the enclosed volume 104 changes states from moving to not moving. At this point the moving average CO2 will follow one of four possibilities as long as at $T_0$ is the CO2 levels are above the nominal atmospheric CO2 threshold value:

1. The moving average CO2 will increase.
2. The moving average CO2 will decrease but not as fast as would be expected given an assumed ACH value for the enclosed volume.
3. The moving average CO2 will exponentially decay within the bounds of tolerance for a given ACH.
4. The moving average CO2 will decrease faster than would be expected given an assumed ACH value for the enclosed volume.

For scenarios one and two above, an additional source of CO2 is present in the system which is likely generated by aerobic respiration from a mammal. For scenario three, this is the expected scenario. Atmospheric CO2 levels are slowly exchanged with the concentrated values inside the enclosed space until equalized under exponential decay. The final scenario would be one in which either door or window or other opening changes the ACH value of the enclosure.

In step 207, the system determines whether the current CO2 level is greater than 450 PPM, which is the ambient threshold. If the CO2 level is not greater than 450 PPM, the system enters sleep mode in step 205.

In step 211, the system determines whether the CO2 level is not decaying fast enough. In this regard, the system queries whether the CO2 level is greater than a nominal high threshold CO2 decay rate, in one embodiment based on a 10% threshold within which is likely acceptably close to the expected exponential decay. The nominal CO2 decay rate is determined from a combination of experimentally determined values and researched values. Further, the nominal CO2 decay rate may be tailored over time for particular enclosed volumes based on CO2 decay readings in the particular enclosed volumes during performance of the system.

Figure 4:
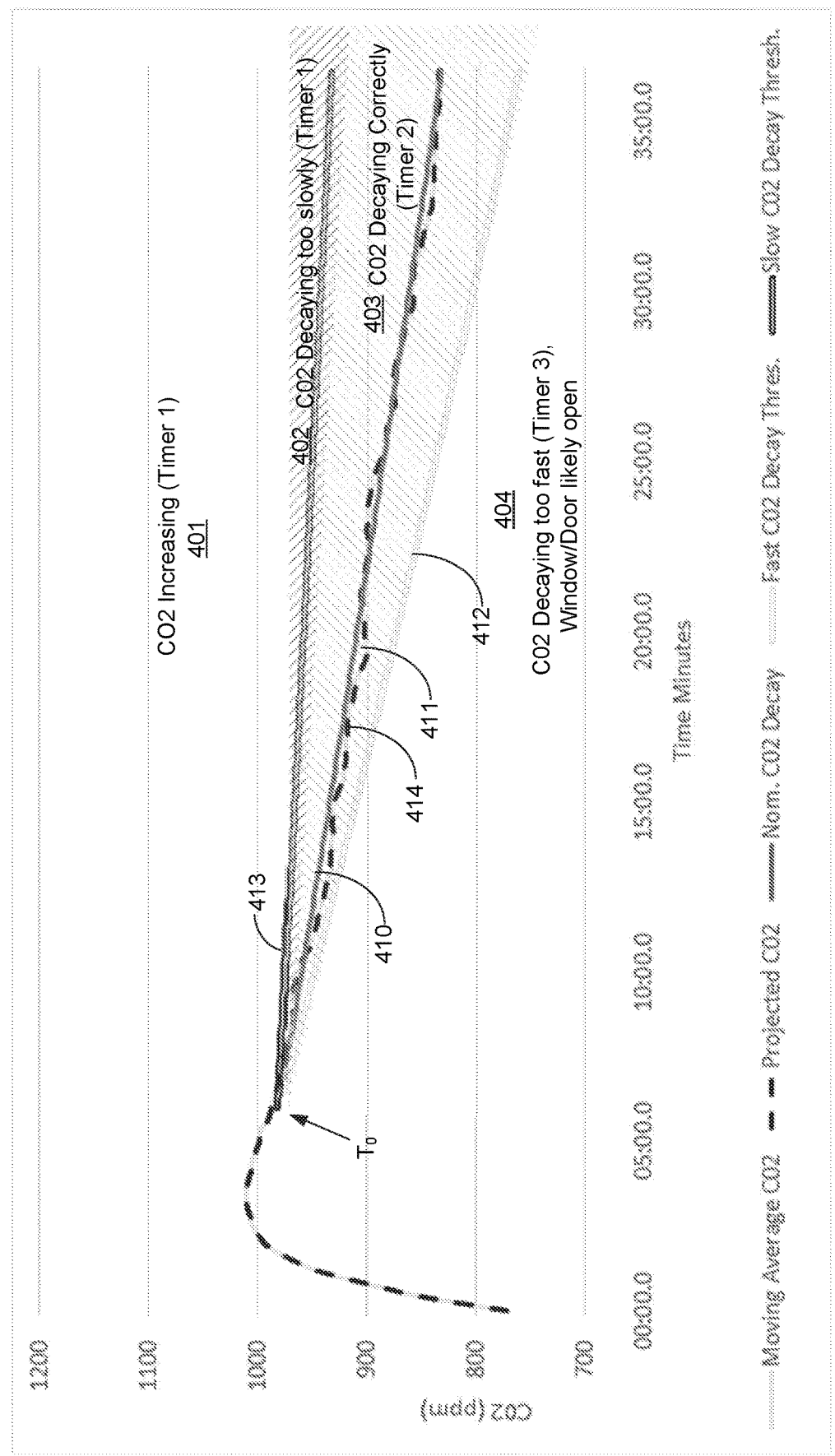
FIG. 4 depicts an exemplary nominal CO2 decay rate compared with test data.

FIG. 4 depicts an exemplary nominal CO2 decay rate compared with test data, the test data obtained in a test of a full sized sedan with a 450 ppm threshold. To on the chart of FIG. 4 indicates when the enclosed volume stopped moving. A moving average CO2 line 414 plots the moving CO2 average as discussed herein. The moving average generally only changes a couple of PPM in a 15 second interval. A projected CO2 line 411 plots the projected CO2 decay rate. (The projected CO2 line 411 tracks the moving average CO2 line 414 in the example of FIG. 4.)

The moving average decay rate has to be consistently above the projected rate prediction for each iteration over a several minute period or the timers will reset. A nominal CO2 decay line 410 plots the nominal CO2 decay for the volume and temperature. A fast CO2 decay threshold line 412 indicates a threshold below which the CO2 level is decaying faster than expected. A slow CO2 decay threshold line 413 indicates a threshold above which the CO2 rate is decaying too slowly, indicating a potentially dangerous situation inside the enclosed vehicle.

FIG. 4 indicates graphically that if the actual decay rate is in the region 401, the CO2 level is increasing, which may indicate that a mammal has been left unattended in the enclosed volume. If the actual decay rate is in the range of the region 402, the CO2 rate is decaying too slowly, which may also indicate that a mammal has been left unattended in the enclosed volume. (Region 401 is essentially a subset of region 402). If the actual decay rate is in the range of the region 403, the CO2 rate is decaying correctly. If the actual decay rate is in the range of the region 404, then the CO2 rate is decaying too fast, which could indicate, for example, that windows or doors are open.

Returning to step 211, if the CO2 rate is not decaying fast enough, then in step 211a the system switches from a sleep mode to an "active" mode, enabling the GSM/GPS and coming out of "deep sleep."

In step 211b, a first timer (Timer1) is incremented and begins timing a possibly dangerous condition due to rising CO2 levels or CO2 levels which are not falling (decaying) fast enough in the enclosed volume 104. A second timer (Timer2) and a third timer (Timer3) are cleared.

In step 211c, the system queries whether the first timer (Timer 1) exceeds a predetermined value, a stabilization value which is five minutes in one embodiment. The stabilization value is a duration determined through testing to sufficient such that CO2 levels have been given time to stabilize into a uniform decay curve.

After the first timer exceeds the stabilization value, in step 211d, the system determines whether the enclosed volume 104 is moving or running. If the enclosed volume 104 (e.g., automobile), is running or moving, then the method continues at step 231 (FIG. 2C), as further discussed below with respect to FIG. 2C.

Figure 2B:
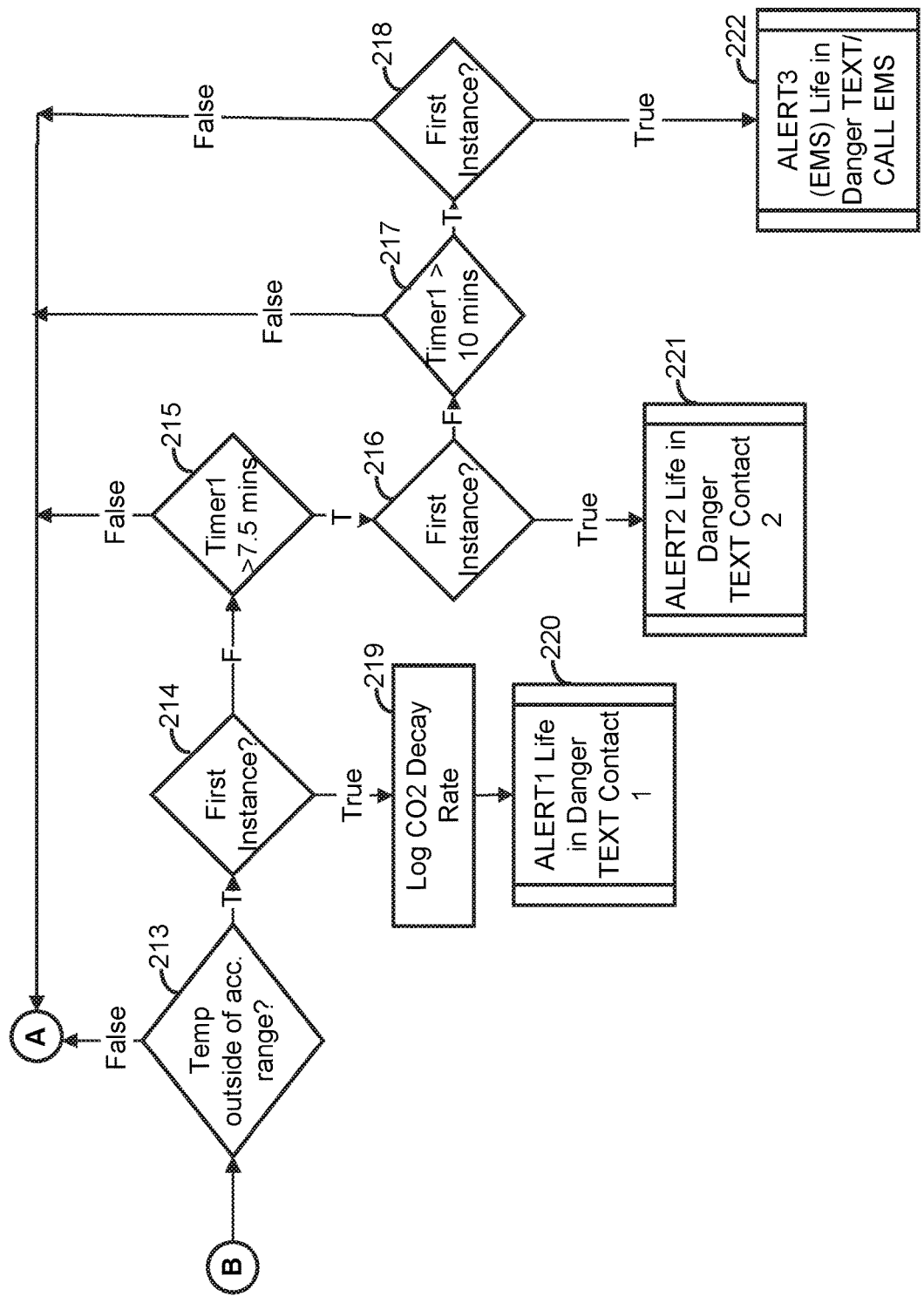
FIG. 2B is a continuation of the flow chart of FIG. 2A.
Figure 2C:
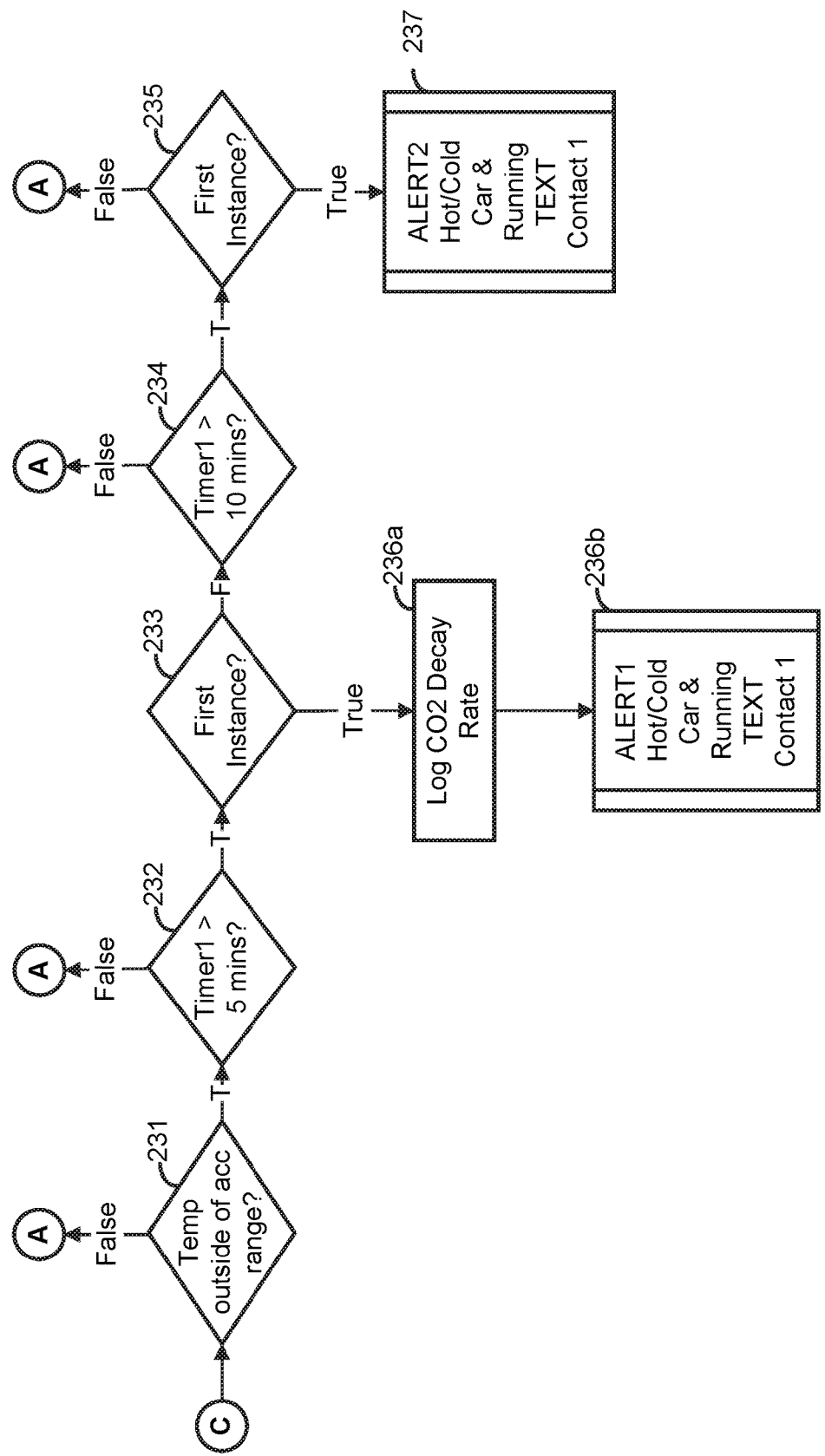
FIG. 2C is a continuation of the flow chart of FIG. 2A.

If the enclosed volume is not moving or running, then the method proceeds at step 213 (FIG. 2B).

Returning to step 211, if it is false that the CO2 is not decaying fast enough (i.e., the CO2 level is decaying too fast), then in step 212, the system determines whether the CO2 level is less than 90% of the nominal value. (The 90% of nominal value is a boundary that is adjustable in other embodiments.) If the CO2 level is less than 90% of the nominal value, then in step 212a a third timer (timer3) is incremented, and timer1 and timer2 are cleared.

In step 212b, the system queries whether the third timer exceeds a predetermined value, a stabilization value which is five minutes in one embodiment. The stabilization value is a duration determined through testing to sufficient such that CO2 levels have been given time to stabilize into a uniform decay curve. If the third timer does not exceed the stabilization value, then the system enters sleep mode in step 205. If the third timer does exceed the stabilization value, then in step 212c, the system queries whether the window/door alerts are enabled. This step asks essentially whether the user has configured the system to request such alerts. If the window/door alerts are enabled, then the method continues at step 250 on FIG. 2D. If the window/door alerts are not enabled, then the method continues at step 212e (FIG. 2A), as further discussed herein.

Referring back to step 212, in one embodiment if the CO2 level not less than 90% of the nominal value, then in step 212d, a timer 2 is incremented and timer1 and timer3 are cleared. In step 212e, if timer2 or timer3 are greater than a predetermined duration (15 minutes in the illustrated embodiment), and there are no alerts in the system, then in step 212f GSM and GPS are disabled, and the system enters a deep sleep mode.

In step 212g, if this is the first instance that the system enters a deep sleep mode, then in step 212h, the CO2 decay rate is logged, and the method continues at step 205. If this is not the first such instance, then the method continues at step 205.

Referring to FIG. 2B, in step 213 the system queries whether the temperature is outside of an acceptable range. If the temperature is not outside of the acceptable range (less than sixty degrees Fahrenheit or greater than ninety degrees Fahrenheit in one embodiment), then the method resumes at step 205 on FIG. 2A.

If the temperature is outside of the acceptable range, in step 214, the system queries whether this is the first instance of such a condition. If it is the first instance, then in step 219, the CO2 decay rate is logged for future use. In this regard, aggregated logged values may be used to characterize the enclosed volume (e.g., vehicle) to increase algorithm sensitivity in the future. In step 220, a first alert that a life is in danger is sent.

In one embodiment, the first alert is in the form of a text to a first contact, e.g., the expected driver of the vehicle.

Returning to step 214, it is not the first instance, then in step 215, the system queries whether the first timer has exceeded 7.5 minutes. This time period is exemplary, and other time periods may be used in other embodiments. The 7.5 minute delay gives the recipient of the first alert an opportunity to address the situation before another alert is sent out.

If the time period has not exceeded 7.5 minutes, then the system returns to sleep mode in step 205 (FIG. 2A). If the time period has exceeded 7.5 minutes, then in step 216, the system queries whether this is the first instance of such a condition. If it is the first instance, then in step 221, a second alert that a life is in danger is sent to a second contact.

In one embodiment, the second alert is in the form of a text to the second contact.

Returning to step 216, if not the first instance, then the system queries whether the first timer has exceeded ten minutes. This time period is exemplary, and other time periods may be used in other embodiments.

If the time period has not exceeded ten minutes, then the system returns to sleep mode in step 205 (FIG. 2A). If the time period has exceeded ten minutes, then in step 218, the system queries whether this is the first instance of such a condition. If it is the first instance, then in step 222, a third alert is sent.

In one embodiment, the third alert is in the form of a text or call to the Emergency Management System (e.g., 911).

Returning to step 218, if it is not the first instance, then the system returns to a sleep mode in step 205 (FIG. 2A).

Returning to step 211d (FIG. 2A), if the CO2 level not decaying fast enough, but the car is moving/running, then in step 231 (FIG. 2C), In step 231, the system queries whether the temperature is outside of a nominal range. In one embodiment, the nominal range is greater than sixty degrees Fahrenheit and less than ninety degrees Fahrenheit. If the temperature is within the nominal range, then the system returns to a sleep mode per step 205 (FIG. 2A). If the temperature is outside of the nominal range, then in step 232, the system queries whether the first timer has exceeded a predetermined value, five minutes in this embodiment. If the first timer has not exceeded the predetermined value, then the system returns to a sleep mode for some short duration, on the order of 15 seconds in one embodiment, per step 205 (FIG. 2A)

If the first timer has exceeded the predetermined value, then in step 233, the system queries whether this is the first instance of such a condition. If it is a first instance, then in step 236a, the CO2 rate is logged, and in step 236b, the user is alerted to the condition via a first alert. In one embodiment, the first alert is a text sent to a first contact.

If step 233 determines that this is not the first instance, then in step 234, the system queries whether the first timer has exceeded another predetermined value, ten minutes in this embodiment. If the first timer has not exceeded the predetermined value, then the system returns to a sleep mode for some short duration, on the order of 15 seconds in one embodiment, per step 205 (FIG. 2A).

If the first timer has exceeded the predetermined value, then in step 235, the system queries whether this is the first instance of such a condition. If it is a first instance, then in step 237, the user is alerted to the condition via a second alert. In one embodiment, the second alert is another text sent to the first contact.

In FIG. 2D, step 250, if the window/door alerts are enabled (per step 226, FIG. 2A), then the system queries whether the third timer has exceeded a predetermined value, five minutes in this embodiment. If the third timer has not exceeded the predetermined value, then the system returns to a sleep mode for some short duration, on the order of 15 seconds in one embodiment, per step 205 (FIG. 2A).

If the third timer has exceeded the predetermined value, then in step 251, the system queries whether this is the first instance of such a condition. If it is a first instance, then in step 252, the CO2 rate is logged, and in step 253, the user is alerted to the condition via a first alert. In one embodiment, the first alert is a text sent to a first contact.

In addition to the alerts as discussed herein, the system in some embodiments may also be used as a panic button/SOS call, enabling a person within the enclosed volume to send a distress alert.

Figure 3:
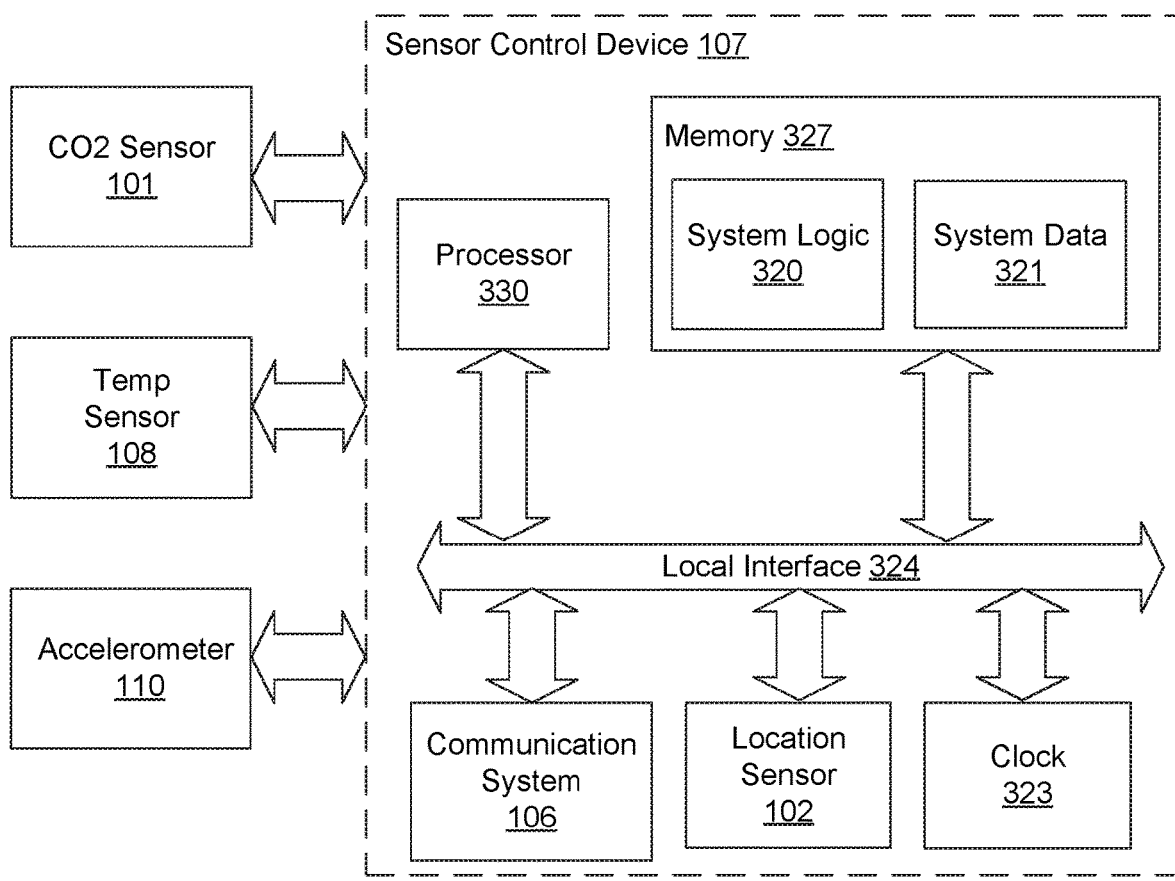
FIG. 3 depicts a CO2 sensor and sensor control device according to an exemplary embodiment of the present disclosure.

FIG. 3 depicts a CO2 sensor 101, temp sensor 108, accelerometer 110, and sensor control device 107 according to an embodiment of the present disclosure. The sensor control device 107 comprises system logic 320 and system data 321. In the exemplary sensor control device 107, system logic 320 and system data 321 are shown as stored in memory 327. The system logic 320 and system data 321 may be implemented in hardware, software, or a combination of hardware and software.

The sensor control device 107 also comprises a processor 330, which comprises a digital processor or other type of circuitry configured to run the system logic 320 by processing the system logic 320, as applicable. The processor 330 communicates to and drives the other elements within the sensor control device 107 via a local interface 324, which can include one or more buses. When stored in memory 327, the system logic 320 and the system data 321 can be stored and transported on any computer-readable medium for use by or in connection with logic circuitry, a processor, an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The system logic 320 executes the processes described herein with respect to FIGS. 2A, 2B, 2C, and 2D. The system data 321 comprises the data gathered by the CO2 sensor 101, temperature sensor 108, power supply 109, sensor control device 107, communication system 106, location sensor 102, and accelerometer 110.

Referring to FIG. 3, the communication system 106 may communicate with an input device (not shown), for example, a keyboard, a switch, a mouse, and/or other type of interface, which can be used to input data from a user of the system 100. The communication system 106 may also communicate with or comprise a display device (not shown) that can be used to display data to the user. The communication system 106 may also or alternatively communicate with or comprise a personal digital assistant (PDA), computer tablet device, laptop, portable or non-portable computer, cellular or mobile phone, or the like. The communication system 106 may also or alternatively communicate with or comprise a non-personal computer, e.g., a server, embedded computer, microprocessor, or the like. The communication system 106 may also or alternatively comprises a local interface (not shown) for communication with a key fob or button or similar device that the user could use to deactivate an alert; for example, if the user receives and alert and knows that no one has been left in the enclosed volume.

The communication system 106 further may interface with or comprise a GPS receiver or a cellular network.

The communication system 106, location sensor 102, and clock 323 are shown as part of the sensor control device 107 in the exemplary embodiment of FIG. 3. In other embodiments, the communication system 106, location sensor 102, and/or clock 323 may be outside of the sensor control device and/or part of the CO2 sensor or other sensors.

The invention claimed is:

1. A method for detecting a mammal in a volume with a CO2 detection system, the method comprising:
    positioning a CO2 sensor to sample a CO2 level within the volume;
    when the volume is static, incrementing a timer;
    when the timer is greater than a stabilization value, querying the CO2 sensor and determining whether an obtained CO2 decay rate is outside of an acceptable range;
    when the obtained CO2 decay rate is outside of an acceptable range, determining whether a temperature in the volume is within an acceptable range;
    when the temperature in the volume is outside of the acceptable range, determining whether the CO2 level is not decaying fast enough; and
    when the CO2 level is not decaying fast enough, sending one or more notifications to one or more potential responders.

2. The method of claim 1, where the stabilization value comprises a duration sufficient such that the CO2 level has been given time to stabilize into a uniform decay curve.

3. A method for detecting a mammal in a volume with a CO2 detection system, the method comprising:
    querying a CO2 sensor, the CO2 sensor sampling the CO2 concentration within the volume, and
    obtaining an obtained CO2 decay rate within the volume;
    determining whether a temperature in the volume is within an acceptable range;
    when the temperature in the volume is outside of the acceptable range, determining whether the CO2 level is not decaying fast enough, and
    when the CO2 level is not decaying fast enough, sending one or more notifications to one or more potential responders.

4. The method of claim 3, wherein the step of determining whether the CO2 level is not decaying fast enough comprises querying whether the CO2 level is greater than a nominal high threshold CO2 decay rate.

5. The method of claim 4, wherein the nominal high threshold CO2 decay rate is based on a 10% threshold within which is acceptably close to an expected exponential decay for the volume.

* * * * *